United States Patent [19]

Koletar et al.

[11] 4,358,451
[45] Nov. 9, 1982

[54] PYRIMIDO- AND IMIDAZO-PYRIDOINDOLE DERIVATIVES

[75] Inventors: Gabor I. Koletar, Berkeley Heights, N.J.; Jonathan R. Frost, Palaiseau, France; Regis DuPont, Paris, France; Patrick Lardenois, Bourg la Reine, France; Claude Morel, Massy, France; Henry Najer, Paris, France

[73] Assignee: Synthelabo, Paris, France

[21] Appl. No.: 112,238

[22] Filed: Jan. 15, 1980

[30] Foreign Application Priority Data

Apr. 26, 1979 [FR] France .................... 79 10653

[51] Int. Cl.³ ................ C07D 471/14; A61K 31/505
[52] U.S. Cl. .................................. 424/251; 424/256; 544/247; 548/302; 546/86; 546/87
[58] Field of Search ............. 424/251, 256; 544/247; 548/302

[56] References Cited

FOREIGN PATENT DOCUMENTS 2604989 8/1976 Fed. Rep. of Germany ...... 548/302

OTHER PUBLICATIONS

DeStevens et al., "J. Org. Chem.," vol. 28, 1963, pp. 3210-3212.

Primary Examiner—Donald G. Daus
Assistant Examiner—James H. Turnipseed
Attorney, Agent, or Firm—Wegner & Bretschneider

[57] ABSTRACT

Pyrimido- and imidazo-pyridoindole derivatives, in the form of racemates or optically active isomers, of formula:

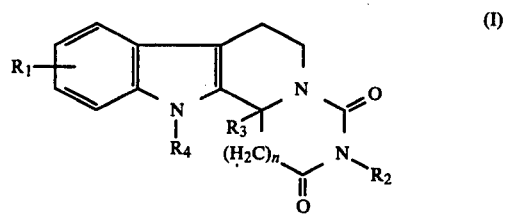

(I)

in which $n=0$ or 1, $R_1=H$, Hal, alkyl or alkoxy or $CF_3$, $R_2=H$, alkyl, cycloalkyl-alkyl, cycloalkyl, N,N-dialkylaminoalkyl or phenyl, $R_3=H$ or alkyl and $R_4=H$, alkyl or benzyl are useful as anti-anoxia or psychotropic agents in therapy. They are prepared by cyclizing a compound of formula:

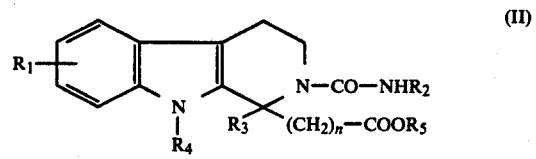

(II)

wherein $R_5$ is alkyl, by heating it in an acidic medium, such as ethanolic hydrogen chloride.

7 Claims, No Drawings

PYRIMIDO- AND IMIDAZO-PYRIDOINDOLE DERIVATIVES

The present invention relates to pyrimido- and imidazo-pyridoindole derivatives, in the form of racemates or enantiomers, and their use in therapy.

The pyrimido- and imidazo-pyridoindole derivatives of the invention have the formula

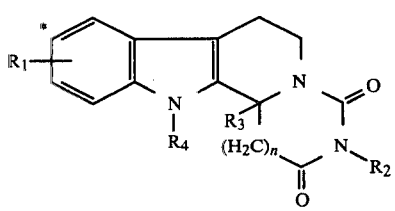

in which n is 0 or 1, the asterisk denotes the 9-position C-atom when n is 1, $R_1$ is a hydrogen or halogen atom, or an alkyl, alkoxy or trifluoromethyl radical ($CF_3$), $R_2$ is a hydrogen atom, a linear or branched alkyl radical, a cycloalkyl-alkyl radical, a cycloalkyl radical, a dialkylaminoalkyl radical or a phenyl radical which optionally carries a halogen atom, $R_3$ is a hydrogen atom or an alkyl radical and $R_4$ is a hydrogen atom, an alkyl radical or a benzyl radical, the alkyl and alkoxy radicals having from 1 to 4 carbon atoms and the cycloalkyl radicals having from 3 to 6 carbon atoms, with the exception of the compounds in which n=1, $R_1$=H, $R_2$=H or n—$C_4H_9$ and $R_3$ and $R_4$=H, but including pharmaceutically acceptable salts of these compounds especially acid addition salts.

The above pyrimido- and imidazo-pyridoindole derivatives are herein referred to for brevity as "the therapeutic compounds". They have an asymmetric carbon atom in the 12b-position (n=1) or 11b-position (n=0) and the above definition includes them in the form of the racemates and enantiomers.

A preferred class of the therapeutic compounds is those in which $R_1$ is a hydrogen atom, or a chlorine or fluorine atom, $R_2$ is an alkyl radical having 1 to 4 carbon atoms, $R_3$ is a hydrogen atom or methyl group and $R_4$ is a hydrogen atom or methyl group.

A more preferred class of the above preferred compounds is those in which $R_1$ is a chlorine atom in the 9-position, $R_2$ is a methyl or ethyl group, $R_3$ is a hydrogen atom or a methyl group and $R_4$ is a hydrogen atom.

The invention includes the above-defined therapeutic compounds in the particular context of their use in therapy and especially in the form of a pharmaceutical composition thereof which also contains a pharmaceutically acceptable excipient. This utility is referred to hereinafter.

The invention provides a process for the preparation of the above-defined therapeutic compounds, from a starting compound of general formula (II)

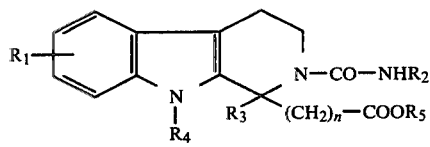

wherein $R_1$, $R_2$, $R_3$, $R_4$ and n are as defined above and $R_5$ represents an alkyl, preferably methyl or ethyl, group by heating in an acidic medium to bring about cyclisation. For the cyclisation the preferred reaction temperature is 50°–150° C., especially 50°–80° C., the preferred acid is hydrogen chloride and the preferred diluent medium is an alcohol, especially ethanol. Most preferably the cyclisation is effected with the aid of hydrogen chloride in an alcoholic medium, at the boiling point of the alcohol.

The therapeutic compounds in which $R_4$ is an alkyl or benzyl radical can be obtained from the therapeutic compounds in which $R_4$ is a hydrogen atom by direct alkylation or benzylation of the nitrogen atom. Furthermore, the therapeutic compounds in which $R_2$ is different from H can also be obtained by direct alkylation of the nitrogen atom of the therapeutic compounds in which $R_2$ is H. A preferred alkylating agent is an alkyl iodide in the presence of a strong base, e.g. sodium hydride.

The starting compounds (II) in which $R_3$=alkyl can be prepared from substituted or unsubstituted tryptamine in accordance with the following scheme, $R_1$, $R_5$ and n being as defined above, to give a compound (II') which is then reacted with an isocyanate $R_2$NCO or (for $R_2$=H) alkali metal cyanate in know manner.

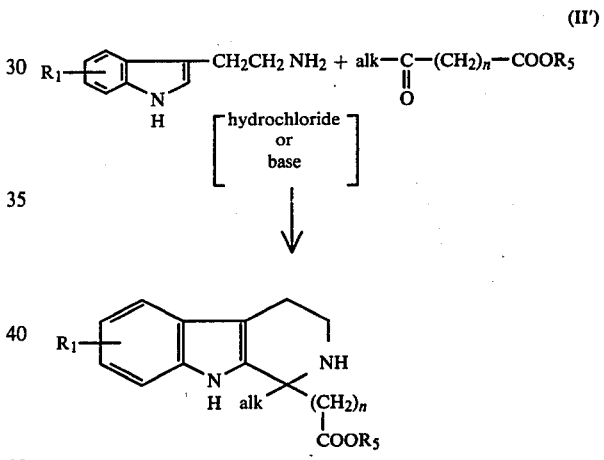

This reaction is described in the literature by J. A. Maclaren, Aust. J. Chem. (1977) 30, 2,045–51.

The starting compounds (II') in which $R_3$=H and n=1 can be prepared from the hydrochloride of substituted or unsubstituted tryptamine in accordance with the following reaction scheme, in which $R_5$ is illustrated as an ethyl radical and $R_1$ is as defined above.

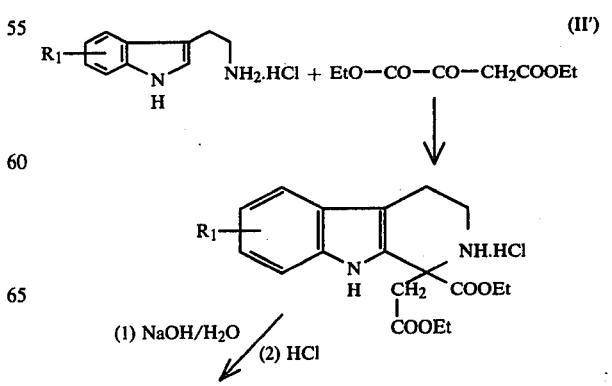

-continued

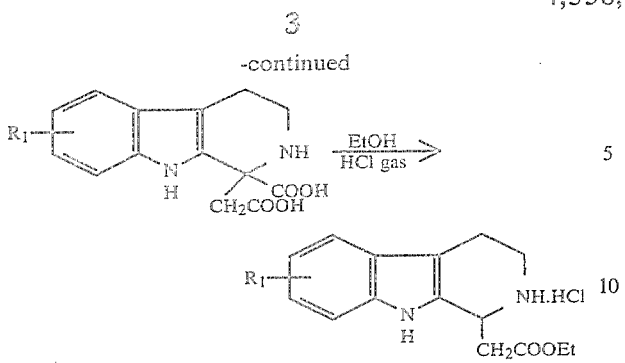

The compound (II') in which $R_1$ is H and n is 1 is described by L. H. Groves and G. A. Swan, J. Chem. Soc. (1952) 650.

The starting compounds (II') in which $R_1$ is different from H are new.

EXAMPLE OF THE PREPARATION OF A COMPOUND (II')

[$R_1=9$—$CH_3$, n=1, $R_3=H$]

1. 52.62 g (0.25 mol) of 5-methyltryptamine hydrochloride are suspended in 250 ml of ethanol and the suspension is heated to the reflux temperature. 57.75 g of 3-ethoxycarbonyl-1,2-dioxo-1-ethoxypropane are suspended in 250 ml of ethanol, and 25 ml of concentrated hydrochloric acid are added dropwise in the course of 10 minutes. The latter suspension is added to the 5-methyltryptamine suspension kept at the reflux temperature. The mixture is allowed to cool overnight. The solvent is removed by evaporation, the residue is dissolved in 400 ml of water and the solution is rendered alkaline with ammonia. After extraction with ethyl acetate, an oil is obtained which is chromatographed on a silica column. After elution with an 8/2 mixture of chloroform and ethanol, an oil is obtained which solidifies on trituration with petroleum ether. After recrystallisation from hexane, the compound obtained

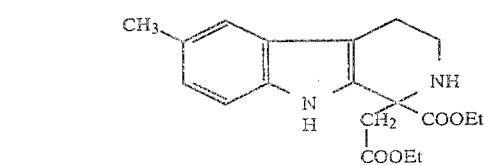

melts at 102°–103° C.

2. 45 g of the above compound are heated under reflux for 20 hours in 450 ml of a 10% strength aqueous solution of NaOH. Concentrated hydrochloric acid (100 ml) is added dropwise, in the course of 30 minutes, to the cooled reaction mixture. The resulting solid is filtered off and dried over $P_2O_5$.

3. 99.6 g of the crude solid obtained above are heated under reflux in a mixture of 250 ml of ethanol and 20 ml of concentrated sulphuric acid for 9 hours. The mixture is left to stand overnight. The ethanol is removed by evaporation and the residual solid is rendered alkaline with ammonia. The basic solution is extracted with 3 times 300 ml of ethyl acetate. The extract is evaporated. An oil is obtained which gives a white solid on trituration with petroleum ether. The solid is filtered off and dried.

After recrystallisation from hexane, the resulting compound (II) melts at 103° C.

The following examples illustrate the invention.

The micro-analyses and the IR and NMR spectra confirm the structure of the compounds.

EXAMPLE 1

2-Methyl-2,3,5,6,11,11b-hexahydroimidazo[1',5':1,2-]pyrido[3,4-b]indole-1,3-dione

[n=0, $R_1=H$, $R_2=CH_3$, $R_4=H$]

1. Ethyl 2-methylaminocarbonyl-2,3,4,9-tetrahydro-1H-pyrido[3,4-b]indole-1-carboxylate.

48.9 g (0.2 mol) of ethyl 2,3,4,9-tetrahydro-1H-pyrido[3,4-b]indole-1-carboxylate in 900 ml of cyclohexane are placed in a round-bottomed flask.

The mixture is stirred and heated to the reflux temperature under a nitrogen atmosphere. A solution of 11.4 g (0.2 mol) of methyl isocyanate in 100 ml of cyclohexane is added dropwise at the boil in the course of 15 minutes. The mixture is heated at the reflux temperature for 3 hours. It is cooled to ambient temperature. The solid is filtered off and washed with cyclohexane. It is dried in vacuo. The compound obtained melts at 158°–162° C.

2. 2-Methyl-2,3,5,6,11,11b-hexahydroimidazo[1',5':1,2]pyrido[3,4-b]indole-1,3-dione.

4.4 g (0.0146 mol) of the compound obtained above and 400 ml of ethanol are placed in a round-bottomed flask. The solid is dissolved by heating. 28 ml of ethanol saturated with hydrogen chloride are added. The mixture is heated at the reflux temperature for 1 hour 30 minutes. It is left to stand overnight. The solid is filtered off and washed with ice-cooled ethanol and the compound is recrystallised from nitromethane in the presence of carbon black.

The solid is isolated and dried in vacuo at 110° C. for 8 hours.

The compound obtained melts at 254°–256° C.

EXAMPLE 2

9-Chloro-3-methyl-1,2,3,4,6,7,12,12b-octahydropyrimido[1',6':1,2]pyrido[3,4-b]indole-2,4-dione

[n=1, $R_1=9$—Cl, $R_2=CH_3$, $R_3=H$, $R_4=H$]

10 g of ethyl 6-chloro-2,3,4,9-tetrahydro-1H-pyrido[3,4-b]indole-1-acetate (prepared according to the patent entitled Pyridoindoles, filed by the Applicant Company on this same day) are placed in a round-bottomed flask and 150 ml of cyclohexane and 2.5 ml (1.9 g) of methyl isocyanate are added. The mixture is heated at the reflux temperature for 1 hour. It is cooled in an ice bath and filtered. This yields a white solid which is taken up in 150 ml of ethanol. The mixture is stirred and ethanol saturated with hydrogen chloride (30 ml) is added. The mixture is heated under reflux for 1 hour. It is allowed to cool and filtered. The solid is recrystallised from ethanol.

Melting point=304° C.

EXAMPLE 3

3-Methyl-1,2,3,4,6,7,12,12b-octahydropyrimido[1',6':1,2]pyrido[3,4-b]indole-2,4-dione

[n=1, $R_1=H$, $R_2=CH_3$, $R_3=H$, $R_4=H$]

1. Ethyl 2-aminocarbonyl-2,3,4,9-tetrahydropyrimido[3,4-b]indole-1-acetate.

26 g (0.088 mol) of ethyl 2,3,4,9-tetrahydro-1H-pyrido[3,4-b]indole-1-acetate hydrochloride are dissolved in 1 liter of hot water. The pH should be 4–5. When the temperature of the reaction medium is 50° C., a solution of 8.7 g (0.13 mol) of sodium cyanate in 150 cm³ of water is added. The reaction medium is kept at 50° C., whilst stirring. It is stirred for 4 hours at 50° C. and left to stand overnight at ambient temperature; the supernatant water is drawn off. 200 cm³ of ether are added, the mixture is stirred, the ether solution is then drawn off and the same operation is repeated. The expected product is very soluble in ether. The ether extracts are combined and washed with acidified water, in order to remove traces of the starting material, and then with water. They are dried over $Na_2SO_4$ and the solvent is evaporated off. This yields an oil which changes into a foam on more thorough drying. The product is used as such in the following step.

2. 1,2,3,4,6,7,12,12b-Octahydropyrimido[1',6':1,2-]pyrido[3,4-b]indole-2,4-dione.

11.1 g of the above compound are dissolved in 250 cm³ of ethanol under reflux. A saturated solution of HCl gas in 55 cm³ of ethanol is added at this temperature. The mixture is kept at the reflux temperature for 5 hours and then left to stand overnight at ambient temperature. The product is filtered off and washed with EtOH and then with ether. It is dried. This yields a product which is very insoluble in organic solvents. After recrystallisation from dimethylformamide, it melts at 365° C.

3. 3-Methyl-1,2,3,4,6,7,12,12b-octahydropyrimido[1',6':1,2]pyrido[3,4-b]indole-2,4-dione.

A 50% strength dispersion of 1.5 g (0.031 mol) of sodium hydride in oil is added to a solution of 8 g (0.031 mol) of the above compound in 300 cm³ of dimethylformamide. The mixture is stirred for 1 hour 30 minutes with the exclusion of moisture, 4.5 g (0.031 mol) of methyl iodide are then added and the reaction medium is left overnight at ambient temperature, whilst stirring.

The inorganic residue is removed by filtration and the filtrate is then evaporated. The residue is taken up in water and this causes it to solidify as a white solid. The latter is recrystallised from ethanol. The pure compound, which is obtained after recrystallisation from methyl ethyl ketone, melts at 246°–248° C.

TABLE

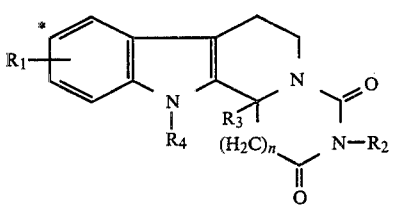

| Compound | R₁ | R₂ | R₃ | R₄ | n | Melting Point (°C.) |
|---|---|---|---|---|---|---|
| 1 | H | CH₃ | H | H | 1 | 246–8 |
| 2 | 9-Cl | CH₃ | H | H | 1 | 304 |
| 3 | H | CH₃ | H | CH₃ | 1 | 228–30 |
| 4 | H | CH₃ | CH₃ | H | 1 | 218 |
| 5 | 9-Cl | CH₃ | CH₃ | H | 1 | 265 |
| 6 | 9-Cl | C₂H₅ | H | H | 1 | 258 |
| 7 | H | n-C₃H₇ | H | H | 1 | 201–2 |
| 8 | H | (CH₂)₂NMe₂ | H | H | 1 | 260 (decomp.) |
| 9 | H | CH₂-◁ | H | H | 1 | 244 |
| 10 | H | i-C₃H₇ | H | H | 1 | 249 |
| 11 | H | H | H | H | 0 | 252–4 |
| 12 | H | CH₃ | H | H | 0 | 254–6 |
| 13 | H | C₂H₅ | H | H | 0 | 194–6 |
| 14 | H | n-C₃H₇ | H | H | 0 | 184–6 |

TABLE-continued

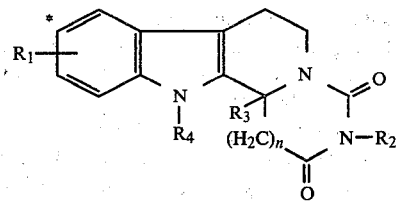

| Compound | R₁ | R₂ | R₃ | R₄ | n | Melting Point (°C.) |
|---|---|---|---|---|---|---|
| 15 | H | i-C₃H₇ | H | H | 0 | 196–8 |
| 16 | H | n-C₄H₉ | H | H | 0 | 172–4 |
| 17 | H | t-C₄H₉ | H | H | 0 | 200–4 |
| 18 | H | C₆H₅ | H | H | 0 | 268–70 |
| 19 | H | p-Cl—C₆H₄ | H | H | 0 | 235–7 |
| 20 | H | CH₃ | CH₃ | H | 0 | 226 |
| 21 | 9-F | CH₃ | CH₃ | H | 1 | >280 |
| 22 | 9-F | C₂H₅ | CH₃ | H | 1 | 240 |
| 23 | 9-F | CH₃ | H | H | 1 | 249–250 |
| 24 | 9-Cl | CH₃ | H | CH₃ | 1 | 266–268 |
| 25 | H | CH₃ | H | CH₂Ph | 1 | 198–9 |
| 26 | 9-F | C₂H₅ | CH₃ | H | 1 | 240 |
| 27 | 9-CH₃ | C₂H₅ | CH₃ | H | 1 | 215 |
| 28 | 9-CH₃ | CH₃ | CH₃ | H | 1 | 262 |
| 29 | 9-CH₃O | CH₃ | CH₃ | H | 1 | 252 |
| 30 | 9-F | CH₃ | CH₃ | H | 1 | >280 |
| 31 | 9-F | CH₃ | H | H | 1 | 249–250 |
| 32 | 9-CH₃O | CH₃ | H | H | 1 | 267–8 |
| 33 | 9-CH₃ | CH₃ | H | H | 1 | 217 |
| 34 | 9-CF₃ | CH₃ | H | H | 1 | 277 |
| 35 | 9-Br | CH₃ | H | H | 1 | 300 |

(* = 9-position C-atom when n = 1)
Ph = phenyl
Me = methyl
ClC₆H₄ = Chlorophenyl The therapeutic compounds were subjected to various pharmacological experiments, namely to the test for the anoxia caused in mice by pressure reduction and to the test for the action on the duration of the sleep induced in curarised rats by sodium 4-hydroxybutyrate.

ANOXIA CAUSED BY PRESSURE REDUCTION

Mice of the CD1 strain are kept in an oxygen-depleted atmosphere produced by creating a partial vacuum (190 mm of mercury, corresponding to 5.25% of oxygen).

The survival time of the animals is noted. This time is increased by agents which are capable of assisting the oxygenation of tissues and in particular of the brain. The compounds studied are administered intraperitoneally in several doses, 10 minutes before the experiment. The percentage increases in the survival time, relative to the values obtained for control animals, are calculated. The mean active dose (MAD), that is to say the dose which increases the survival time by 100%, is determined graphically.

The MAD of the therapeutic compounds, administered intraperitoneally, varies from 0.5 to 20 mg/kg.

ACTION ON THE DURATION OF "SLEEP"

This action was determined by the influence of the therapeutic compounds on the duration of the "sleep" induced in curarised rats by sodium 4-hydroxybutyrate (GBH); the rats are under artificial respiration and their electrocorticographic activity is recorded by means of cortical electrodes.

The therapeutic compounds reduce the total duration of the sleep by 15 to 35%.

The pharmacological study of the therapeutic compounds shows that they are active in the test for the anoxia caused in mice by pressure reduction, whilst being only slightly toxic, and that they exert a significant waking action in the test for the "sleep" induced by sodium 4-hydroxybutyrate.

The therapeutic compounds, because they possess both an anti-anoxia action and a psychotropic action, can be used in therapy for the treatment of vigilance disorders, in particular for combating behavioural disorders which can be attributed to cerebral vascular damage and to cerebral sclerosis encountered in geriatrics, and also for the treatment of epileptic vertigo due to cranial traumatisms, and the treatment of depressive states.

The therapeutic compounds are conveniently administered in pharmaceutical compositions containing the compounds (in free base or salt form) as an active principle, in association with any excipient which is suitable for their administration, preferably their oral or parenteral administration.

The daily posology can range from 10 to 1,000 mg.

We claim:

1. A compound of the formula

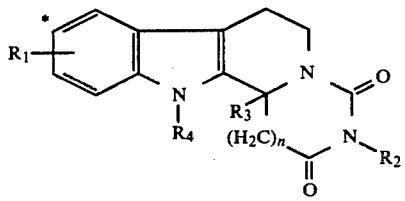

in which n is 0 or 1, R is hydrogen, halogen, alkyl, alkoxy, or trifluoromethyl; $R_2$ is hydrogen, alkyl, cycloalkyl-alkyl, cycloalkyl, N,N-dialkylaminoalkyl or phenyl which is unsubstituted or substituted by halogen, $R_3$ is hydrogen or alkyl; and $R_4$ is hydrogen, alkyl, or benzyl, each alkyl and alkoxy having from 1 to 4 carbon atoms and each cycloalkyl having from 3 to 6 carbon atoms, or a pharmaceutically acceptable salt thereof, except the compounds in which simultaneously $n=1$, $R_2$ is hydrogen, ethyl, n-butyl, or phenyl and $R_1$, $R_3$ and $R_4$ are all hydrogen, said compound being a racemate or optically active isomer.

2. A compound according to claim 1, in which $n=0$ or 1, $R_1$ is hydrogen, chlorine or fluorine; $R_2$ is alkyl having 1 to 4 carbon atoms; $R_3$ is hydrogen or methyl; and $R_4$ is hydrogen or methyl.

3. A compound according to claim 2 which $R_1$ is chlorine in the 9-position, $R_2$ is methyl or ethyl; $R_3$ is hydrogen or methyl; and $R_4$ is hydrogen.

4. A compound according to claim 1, which is 9-chloro-3-methyl-1,2,3,4,6,7,12,12b-octahydropyrimido-[1',6':1,2]pyrido[3,4-b]indol-2,4-dione.

5. A method of treating a patient against anoxia which comprises administering to said patient a therapeutically effective amount of a compound of claim 1, 2, 3, or 4 to provide an anti-anoxia effect.

6. A method of treating a patient against epilepsy which comprises administering to said patient a therapeutically effective amount of a compound of claim 1, 2, 3, or 4 to provide an anti-epileptic effect.

7. A method of treating a patient against depression which comprises administering to said patient a therapeutically effective amount of a compound of claim 1, 2, 3, or 4 to provide an anti-depressive effect.

* * * * *